(12) United States Patent
Kloiber et al.

(10) Patent No.: US 10,603,827 B2
(45) Date of Patent: Mar. 31, 2020

(54) TOOL FOR PRODUCING AN INJECTION DEVICE AND METHOD FOR PRODUCING AN INJECTION DEVICE

(71) Applicant: Gerresheimer Regensburg GmbH, Regensburg (DE)

(72) Inventors: Michael Kloiber, Pfreimd (DE); Michael Wiglenda, Irchenrieth (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 222 days.

(21) Appl. No.: 15/487,946

(22) Filed: Apr. 14, 2017

(65) Prior Publication Data

US 2017/0297239 A1 Oct. 19, 2017

(30) Foreign Application Priority Data

Apr. 18, 2016 (DE) .................. 10 2016 107 131

(51) Int. Cl.

| | |
|---|---|
| *B29C 45/16* | (2006.01) |
| *A61M 5/34* | (2006.01) |
| *A61M 5/178* | (2006.01) |
| *B29C 45/26* | (2006.01) |
| *A61M 5/142* | (2006.01) |
| *B29C 45/14* | (2006.01) |
| *B29L 31/00* | (2006.01) |

(52) U.S. Cl.
CPC ......... *B29C 45/1671* (2013.01); *A61M 5/178* (2013.01); *A61M 5/343* (2013.01); *B29C 45/261* (2013.01); *A61M 5/14244* (2013.01); *A61M 2005/341* (2013.01); *A61M 2207/00* (2013.01); *A61M 2207/10* (2013.01); *B29C 45/14065* (2013.01); *B29C 2045/14139* (2013.01); *B29L 2031/7544* (2013.01)

(58) Field of Classification Search
CPC .. B29C 45/1671; B29C 45/261; A61M 5/178; A61M 5/343; A61M 5/14244
See application file for complete search history.

(56) References Cited

U.S. PATENT DOCUMENTS

| | | | |
|---|---|---|---|
| 5,356,389 A | 10/1994 | Willing | |
| 2017/0014580 A1* | 1/2017 | Oonishi | ............ B29C 45/14065 |

FOREIGN PATENT DOCUMENTS

| | | |
|---|---|---|
| DE | 1 491 743 A | 6/1969 |
| DE | 41 50 099 C1 | 5/1993 |
| DE | 20 2005 006 519 U1 | 9/2005 |
| EP | 0 564 797 B1 | 9/1998 |
| WO | WO 2015/151936 A1 | 10/2015 |

* cited by examiner

*Primary Examiner* — Jacob T Minskey
*Assistant Examiner* — Melody Tsui
(74) *Attorney, Agent, or Firm* — Muncy, Geissler, Olds & Lowe, P.C.

(57) ABSTRACT

A tool and a method for producing an injection device are disclosed. The injection device comprises a hollow needle which is positioned in a basic body of the injection device. The injection device is produced by a two-stage injection process. At least one first slider and a second slider are provided in a tool block. Together with the tool block, the first slider and the second slider form free space, which defines a shape of a pre-injection molded part of the basic body of the injection device.

18 Claims, 6 Drawing Sheets

TOOL FOR PRODUCING AN INJECTION DEVICE AND METHOD FOR PRODUCING AN INJECTION DEVICE

This nonprovisional application claims priority under 35 U.S.C. § 119(a) to German Patent Application No. 10 2016 107 131.5, which was filed in Germany on Apr. 18, 2016, and which is herein incorporated by reference.

BACKGROUND OF THE INVENTION

Field of the Invention

The invention relates to a tool for producing an injection device and to a method for producing an injection device.

Description of the Background Art

German application DE 1 491 743 A1 discloses an injection needle and a method for its production. An anchoring member from a metal plate or disc is attached to the needle. The needle with the anchoring is fastened in a plastic lug by slightly heating the plastic lug. Thus, the anchoring is enclosed by the plastic of the lug and the needle is firmly held in the lug.

German patent DE 41 40 099 C1 discloses a cannula as well as a method for producing such a cannula. The cannula has a needle with a whetted point. At one end of the needle is arranged a cannula holder on which a hose can be pushed on the rear side. The cannula holder is at least partially surrounded by a handle. The cannula holder and the handle are parts produced by a multicomponent injection molding process.

German utility model DE 20 2005 006 519 U1 discloses a curved secure cannula or injection needle. The curvature is used to prevent injuries. The curvature is achieved in that an offset, for example, 10 mm to 20 mm from the needle point, allows precise control of the penetration depth of the needle into a vein.

European patent specification EP 05 64 797 B1, which corresponds to U.S. Pat. No. 5,356,389, and which discloses an infusion needle with a metal cannula and a cylindrical receiving opening of the needle receiving body which is connected thereto. The metal cannula is configured as a functional cannula and is surrounded by a slightly shorter, conical ending and tightly adjoining plastic cannula connected to the receiving opening. The receiving body can be pulled out of the receiving opening. The needle receiving body is configured angled in the transition area between the receiving opening and the plastic cannula, so that the receiving opening of the needle receiving body extends almost parallel to the skin surface.

SUMMARY OF THE INVENTION

It is therefore an object of the invention to provide a tool for producing an injection device with which an injection device can be manufactured cost-effectively and fast. It is also to be avoided that during the manufacturing process plastic particles enter the hollow needle being connected to the basic body and injection-molded around from the basic body.

In an exemplary embodiment, a tool is provided that comprises a tool block; a receptacle for a hollow needle, wherein the receptacle is formed in the tool block; and a first guide for at least one first slider formed in the tool block, and a second guide for a second slider formed in the tool block, wherein the first slider and the second slider together with the tool block substantially determine the shape of a pre-injection molded part of a basic body of the injection device. The second slider, in the state of being inserted into the tool block, can cover an end of the hollow needle inserted in the receptacle.

A method is also provided for producing an injection device which is easy to handle and wherein during the production process it is ensured that no plastic particles enter the hollow needle of the injection device or clog the hollow needle during the injection process of the basic body of the injection device. In addition, the method is intended to reduce the waste in the manufacture of an injection device.

In an exemplary embodiment, the method for producing an injection device includes: inserting a hollow needle into a receptacle in a tool block of a tool; inserting a second slider in an axial direction of the hollow needle, so that the second slider covers and seals an end of the hollow needle positioned in the receptacle; inserting a first slider as far as it rests with a flat front end thereof against a surface of the second slider; forming a pre-injection molded part of a basic body of the injection device by injecting a plastic material into the tool; removing the second slider from the tool, whereby an opening is formed in the pre-injection molded part of the basic body; providing a sealing geometry, so that the opening in the basic body is covered; and closing the opening, by injecting plastic material into the tool.

The method according to an exemplary embodiment provides, as a product, an injection device with a hollow needle (cannula), which can be made of metal or plastic, and a basic body made of plastic. The hollow needle is held in the plastic material of the basic body. The holding of the hollow needle in the basic body is achieved by the hollow needle being coated (surrounded) with the plastic of the basic body by injection molding during the production of the basic body. For example, the hollow needle can have an angle with the axis of the basic body which is less than 180°.

The angle can be an obtuse angle and is in particular between 120° and 170°. According to another advantageous embodiment, the angle is an acute angle and in this case is in particular between 10° and 60°.

The tool according to an exemplary embodiment for producing an injection device comprises a tool block in which a receptacle for a hollow needle is formed. A first guide is formed in the tool block, in which first guide a first slider can be displaced. Likewise, a second guide for at least one second slider is formed in the tool block. The first slider and the second slider, together with the tool block, essentially form the shape of a pre-injection molded part for the basic body of the injection device. The form (shape) of the pre-injection molded part results from a free space being formed between the tool block and the first and second sliders which free space is syringed (extruded) during the injection process by means of the plastic material for the production of the pre-injection molded part of the injection device.

In an embodiment, the second slider pushed into the tool block can enclose an end of the hollow needle inserted into the holder, the rear end of the hollow needle being sealed. A sealing of the rear end of the hollow needle could also be effected by pure touching with the second slider, which has a flat front end. It is only important that the ablation (losing contact) is performed in the axial direction of the injection device, so that no plastic enters the hollow needle laterally.

Furthermore, a plunger can be guided in the second slider which plunger acts on the second end of the hollow needle and pushes it into a predetermined target position, in particular to a precisely defined position, in the tool. An additional effect of the plunger is also that the second end of the hollow needle is sealed by the plunger.

In an embodiment, the first slider has a flat front end which rests over the entire surface against a surface of the second slider when the first slider and the second slider are pushed into the tool.

In an embodiment for the configuration of the tool, a third slider can be provided. After the pre-injection molded part of the basic body of the injection device has been produced by the injection process, the part of the tool containing the pre-injection molded part is rotated. The third slider is then drawn to seal the opening in the pre-injection molded part which opening is formed by the second pusher in the pre-injection molded part. For this purpose, the third slider has formed a sealing geometry. The opening is then closed during a second injection process. The sealing by means of the third slider ensures that no plastic material enters the cavity of the basic body of the injection device.

For effective sealing, a front end of the third slider can be configured such that it rests against a front, inner wall of the basic body. By means of this position of the third slider, the opening is sealed off to the outside.

An embodiment of the invention provides that the first slider can be configured so as to be rotatable in the first guide such that, after the second slider has been removed from the tool, an opening formed by the second slider in the basic body of the pre-injection molded part, basic body is covered from the cavity of the basic body by the rotated first slider. Thus, in a second step (second injection process), the opening in the basic body still present and caused by the second slider can be closed by injection. In this second step of the injection process, the interior of the basic body is not contaminated with plastic.

In order to cover the opening in the basic body of the pre-injection molded part, the first slider can be rotatable about 180° so that a front end of the first slider abuts a front, inner wall of the basic body. By this position of the first slider, the opening is sealed to the outside. For this purpose, the first slider has also formed a sealing geometry.

According to an embodiment according to the invention, the flat front end of the first slider or the third slider can be formed by a slanted surface. The configuration of the front end of the first slider or of the third slider is such that the front end of the first slider or the third slider projects beyond a front edge of the opening in order to reach the sealing of the opening towards the outside.

The method according to an embodiment of the invention for producing an injection device can comprise a step in which a hollow needle is inserted into a receptacle of a tool block of a tool. According to an embodiment, a second slider can be subsequently inserted into the tool in the axial direction of the hollow needle, so that the second slider covers an end of the hollow needle positioned in the receptacle. According to an embodiment, the second slider can enclose and seal the end of the hollow needle positioned in the receptacle.

An embodiment according to the invention of the method according to the invention provides that in the second slider, a plunger can be displaced in the direction of the axis. The plunger acts on the end of the hollow needle so that the needle is pushed into a target position predetermined in the tool block. At the same time, the end of the hollow needle is also sealed with the plunger when the plunger rests at the end of the hollow needle.

Subsequently, the insertion of a first slider is carried out until the first slider rests against a surface of the second slider with a flat front end. As already mentioned, a free space is formed between the first slider and the second slider and the tool body of the tool which free space is filled with the plastic for the pre-injection molded part of the basic body of the injection device during the injection process. In this injection molding process, the hollow needle is also injected or injection-molded into the plastic of the basic body. After completion of the first injection process, the second slider is pulled out of the tool. This creates an opening in the basic body. In order to seal this opening, the first slider can be rotated and inserted, or a third slider can be inserted instead of the first slider so that it rests against the front end of the basic body and covers the opening outwards. Finally, the opening is closed in a second injection molding process. This is carried out by injecting plastic (the same plastic or other plastic) into the tool.

In order to achieve a seal between the first slider and the second slider, the first slider has formed, in one embodiment, a flat front end which, over its entire surface, rests against a surface of the second slider. This is the case when the first slider is pushed into the tool as far as to the second slider, and the surface of the second slider then forms a stop for the first slider.

In an embodiment, the surface of the second slider rests sealingly to the front end of the first slider such that when the plastic is injected into the tool, no plastic passes between the surface of the second slider and the flat front end of the first slider.

For the production of several injection devices in the injection process, the tool is first opened. The hollow needle is inserted into the tool and the tool is closed again. Thereafter, the second slider and the first slider are inserted into the tool and the injection process for the pre-injection molded part is started. Thereafter, the second slider is removed and the first slider is correspondingly rotated and pushed in, or a third slider is inserted instead of the first slider to close the opening outwards. Subsequently, the injection process is continued to the pre-injection molded part and the completed injection molded part is thereby produced. The tool is opened and the completed injection molded part is ejected. The opening in the basic body of the injection device can also be closed by a plastic material different from that of the basic body.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
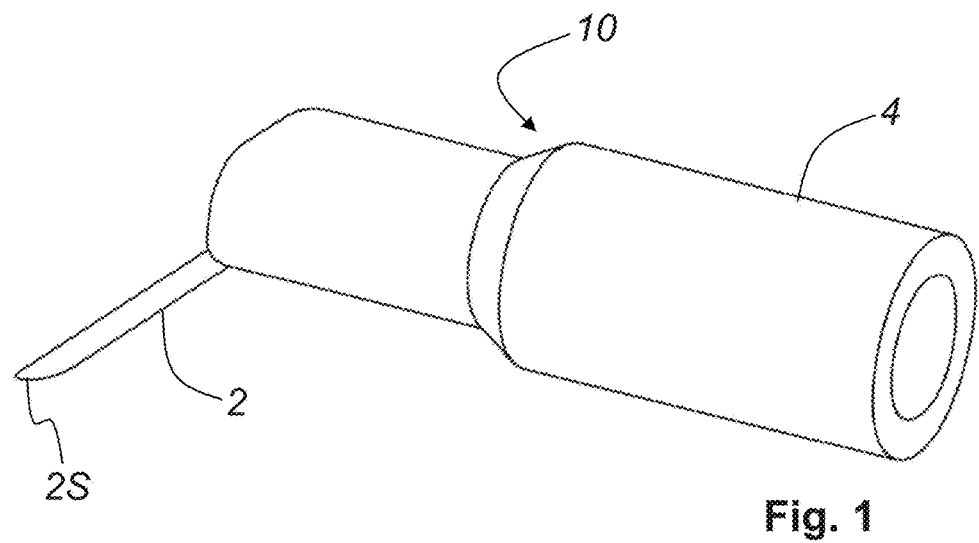
FIG. 1 is a perspective view of an embodiment of an injection device which has been produced by means of the injection molding process according to the invention.

FIG. 1 shows a perspective view of an embodiment of an injection device 10 according to the invention. The injection device 10 comprises a basic body 4 in which a hollow needle 2 is fastened. The hollow needle 2 has a free, pointed end 2S, which can be inserted into a vein or into the body of a person to be treated.

Figure 2:
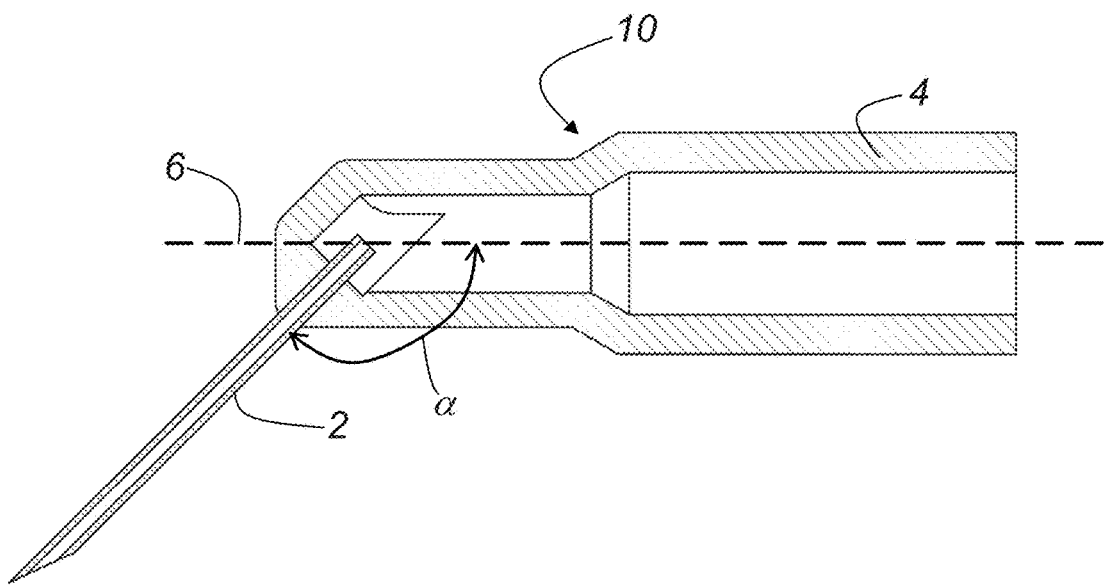
FIG. 2 is a sectional view of the injection device shown in FIG. 1.

FIG. 2 shows a sectional view of an embodiment of the injection device 10 according to the invention along an axis 6. In the injection process, the basic body 4 and in the basic body 4 a cavity 5 is formed. An end 2E of the hollow needle 2 also extends into the cavity 5. The plastic material of the basic body 4 is injection-molded around the hollow needle 2 and the hollow needle 2 is thereby held on or in the basic body 4. In the embodiment shown here, the hollow needle 2 is inclined relative to the axis 6 by an obtuse angle α. The angle α is less than 180°. More preferably, this obtuse angle α is between 120° to 170°. The arrangement according to the invention or fastening of the hollow needle 2 in the basic body 4 ensures that the basic body 4 rests on the body surface of the patient or the person to be treated when the hollow needle 2 is inserted into the vein or into the body of a person to be treated. By means of this advantageous embodiment it can be ensured that no injury or impairment occurs even when the patient is moving by means of the hollow needle. The configuration of the injection device 10 according to the invention significantly improves the wearing comfort of the injection device 10. The basic body 4 of the injection device 10 has an access opening 11, via which, for example, infusion material or medicaments can be supplied to the cavity 5 of the injection device 10.

Figure 3:
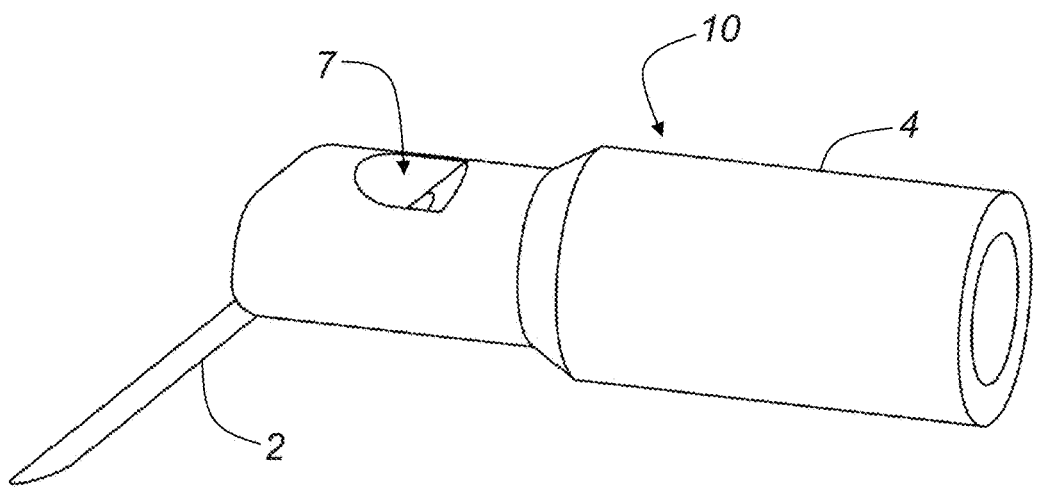
FIG. 3 is a perspective view of the injection device, in which the opening for the access of the second slider can also be seen in the base part.

FIG. 3 shows a perspective view of the injection device 10 according to the invention in a production stage in which the opening 7 can also be seen in the basic body 4 of the injection device 10, via which opening the end 2E of the hollow needle 2 (see FIG. 4) is sealed.

Figure 4:
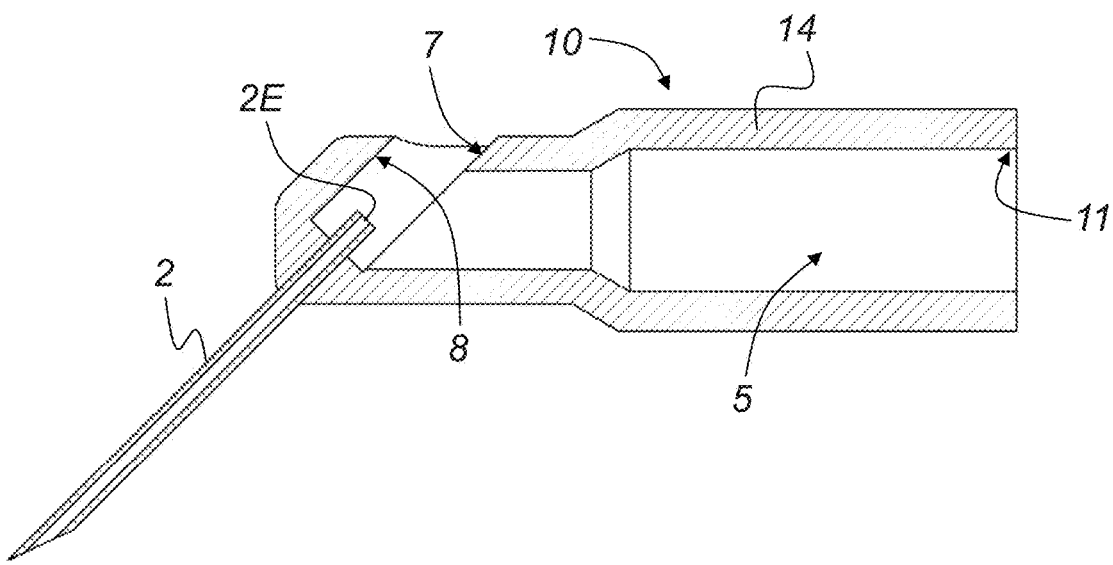
FIG. 4 is a sectional view of the perspective view of the injection device shown in FIG. 3.

In the embodiment shown in FIG. 4, it can be seen that the opening 7 in the basic body 4 extends as far as to the end 2E of the hollow needle 2. The opening 7 extends as far as to the cavity 5 of the basic body 4.

Figure 5:
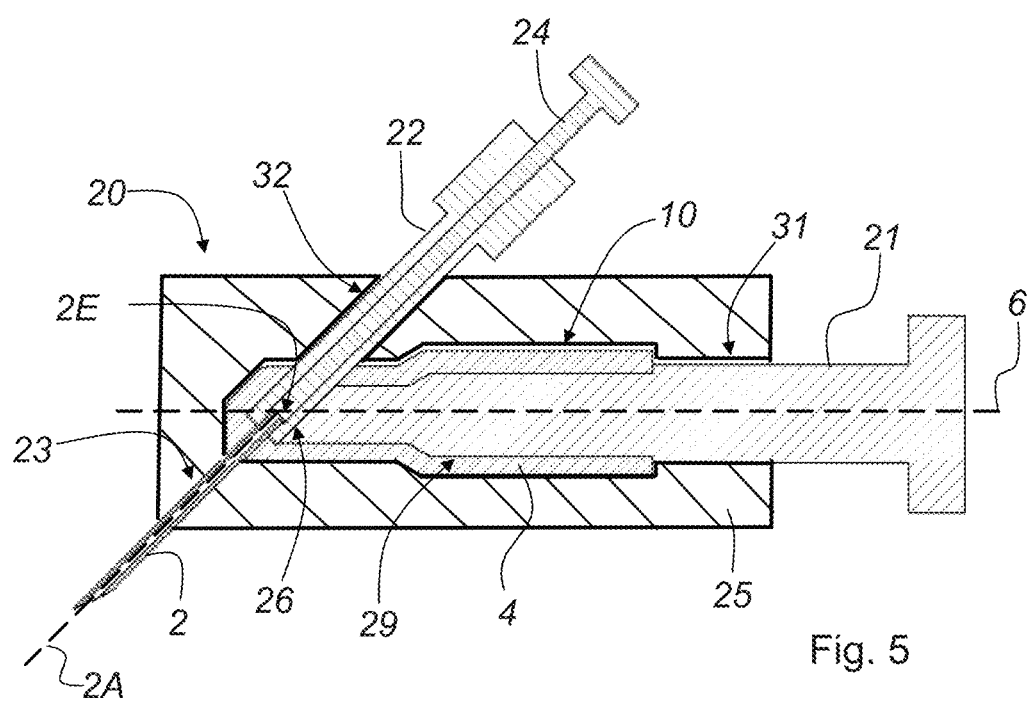
FIG. 5 is a sectional view of the tool for producing the injection device.

FIG. 5 shows a schematic view of the tool 20 for the production of the injection device 10 according to the invention. The tool 20 is shown in section in order to show the first slider 21 and the second slider 22 required for the formation of the injection device 10 with regard to their cooperating relationship. The tool 20 includes a tool block 25 in which a receptacle 23 for the hollow needle 2 is formed. Furthermore, a first guide 31 for the at least one first slider 21 is formed in the tool block 25. Likewise, a second guide 32 for the second slider 22 is formed in the tool block 25. When the first slider 21 and the second slider 22 are pushed completely into the tool block 25, they together with the tool block 25 form a free space 29, which, when syringed (extruded) with the plastic material, forms the pre-injection molded part 14 of the basic body 4 according to the invention for the injection device 10.

According to the embodiment shown here, a plunger 24 is guided in the second slider 22. The plunger 24 can serve to push the hollow needle 2 from the plunger 24 to an exactly defined position (target position) in the tool 20. The plunger 24 acts in the direction of the axis 2A of the hollow needle 2. An additional effect of the plunger 24 is also that it seals the end 2E of the hollow needle 2 since plunger 24 rests on the end 2E of the hollow needle 2.

According to an embodiment of the invention, the second slider 22 inserted completely into the tool block 25 surrounds the hollow needle 2 at its end 2E. The inserted plunger 24 thus also ensures that no plastic material passes into the hollow needle 2 during the injection process of the free space 29, and at the same time, a detaching (losing contact) of the second slider 22 is also prevented. The first slider 21 is pushed along the axis 6 of the injection device 10 until it rests with a flat front end 21E over an entire surface on a surface 26 of the second slider 22.

Figure 6:
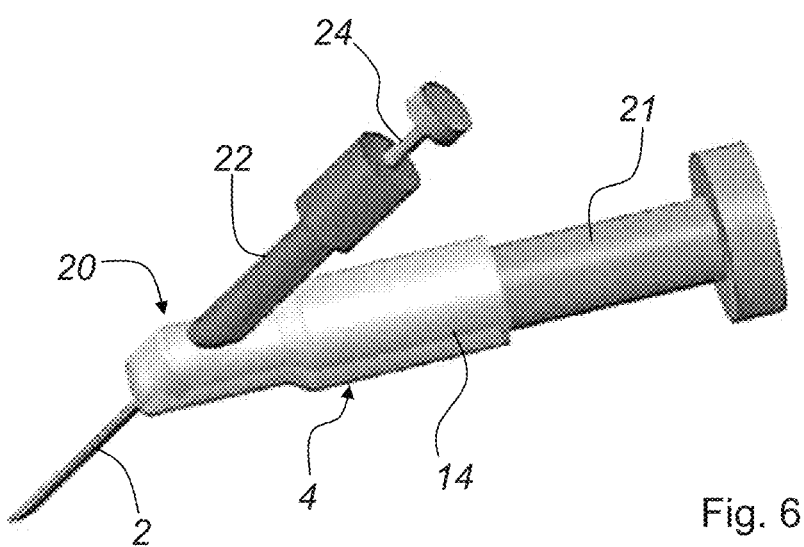
FIG. 6 is a perspective view of the positioning of the first and second sliders in the tool with respect to the basic body of the injection device.

FIG. 6 shows a perspective view of the arrangement of the first slider 21 and the second slider 22 with respect to the basic body 4 of the injection device 10. The embodiment of the second slider 22 with the plunger 24 is likewise shown here. The tool body 25 has been omitted in this illustration in order to obtain a better impression of the arrangement of the first slider 21 and the second slider 22. In this case, the plunger 24 is still completely inserted into the second slider 22 and rests on the end 2E of the hollow needle 2. Hence, in FIG. 6, the first stage of the injection molding process is shown, with which essentially the pre-injection molded part 14 of the basic body 4 of the injection device 10 is formed, and the hollow needle 2 is already firmly anchored in the basic body 4 by injection molding with plastic around hollow needle 2.

Figure 7:
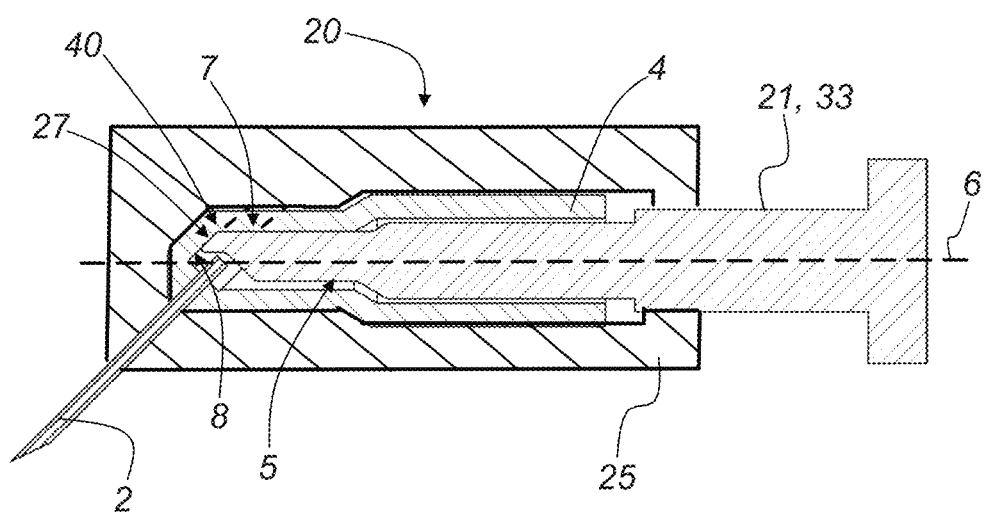
FIG. 7 is a sectional view of the tool and the positioning of the first slider for the final injection molding of the basic body.

FIG. 7 shows the situation in which the second slider 22 has already been removed from the tool block 25. By removing the second slider 22, the opening 7 in the pre-injection molded part 14 of the basic body 4 of the injection device 10 becomes free. In FIG. 7, the opening 7 is shown only as a dashed line, since it has already been closed by a second injection process. In the embodiment shown here, after removal of the second slider 22 from the tool 20 or tool block 25, a third slider 33 is inserted into the tool block 25 and thus into the pre-injection molded part 14. The third slider 33 has formed a sealing geometry 40 which covers the opening 7 in the basic body 4.

An embodiment provides that the first slider is not removed, but merely rotated. For example, the first slider 21 is rotated about an angle of 180°. After the rotation, the first slider 21 is inserted along the axis 6 as far as into the tool block 25, and the sealing geometry 40 covers the opening 7 in the basic body 4.

The sealing geometry 40 can be configured such that a front end 27 of the first slider 21 or the third slider 33 rests (abuts) against a front, inner wall 8 of the basic body 4. This ensures that the opening 7 is sealed off from the outside and no plastic material can enter the cavity 5 of the basic body 4 during a subsequent injection process.

Figure 8:
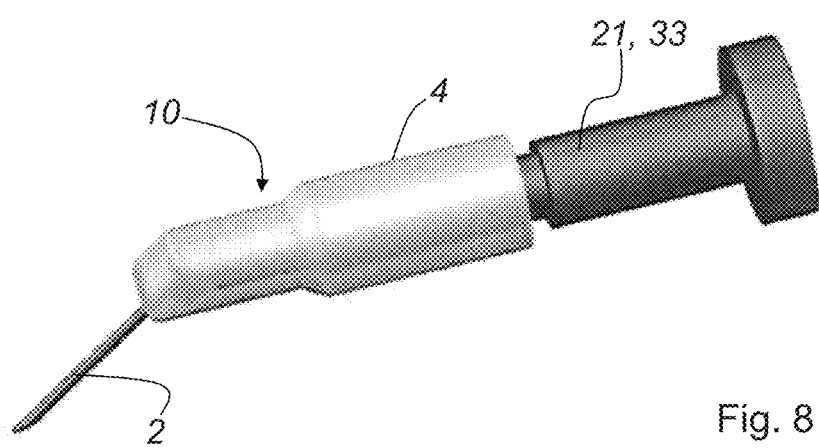
FIG. 8 is a perspective view of the positioning of the first slider in the tool with respect to the completely injected basic body of the injection device.

FIG. 8 shows the situation in which the tool block 25 is removed and the opening 7 is already closed with further plastic material by the second injection process. The first slider 21 or also the third slider 33 is still positioned in the basic body 4 of the injection device 10. The closing of the opening 7 can be effected in the second step of the injection process with the same plastic material as that of the basic body 4, or another plastic material, which accordingly adheres to the plastic material of the basic body 4 of the first injection process, can be used.

Figure 9:
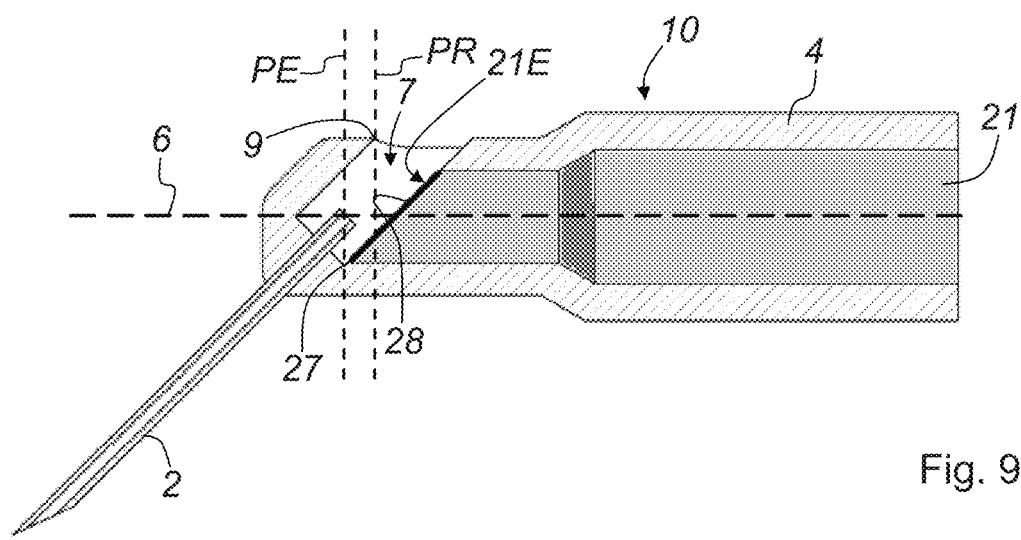
FIG. 9 is a sectional view of the basic body and the geometry of the front end of the first slider.

FIG. 9 shows a sectional view of the basic body 4 of the injection device 10 produced by the first injection process and of the hollow needle 2 fastened in the basic body 4. The second slider 22 is already removed so that the opening 7 becomes free. The opening 7 extends as far as to the end 2E of the hollow needle 2. The first slider 21 is still in the position for the first injection process. The flat front end 21E of the first slider 21 has a slanted surface 28. The front free end 27 of the first slider 21 protrudes a front edge 9 of the opening 7. The front free end 27 of the first slider 21 is at a position PE, and the front edge 9 of the opening 7 is at the position PR. From FIG. 9, it can be clearly seen that the positions PE and PR are clearly displaced from one another in the direction of the axis 6.

Figure 10:
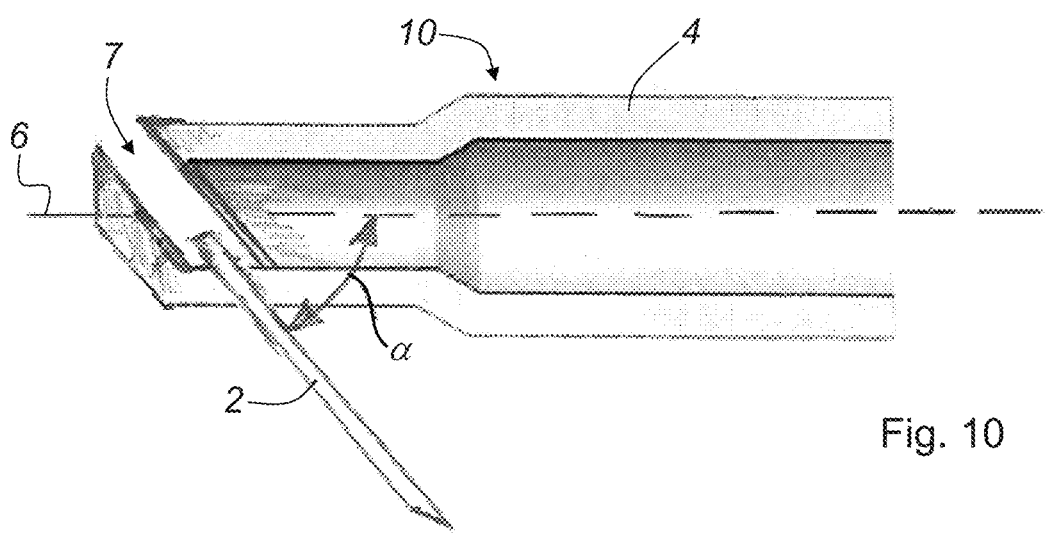
FIG. 10 is an embodiment of the injection device, which can be produced with the method according to the invention or with the tool according to the invention.

FIG. 10 shows a further possible embodiment of the injection device 10 according to the invention in section. Here again, the opening 7 is not yet closed by the second injection process. The hollow needle 2 fastened in the basic body 4 of the injection device 10 is inclined by an angle α with respect to the axis 6, and the angle α forms an acute angle. The angle α can be between 10° and 60°.

Figure 11:
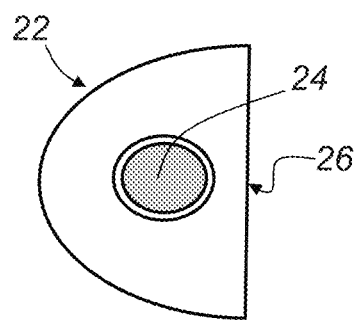
FIG. 11 is a sectional view perpendicular to the axis of the second slider.
Figure 13:
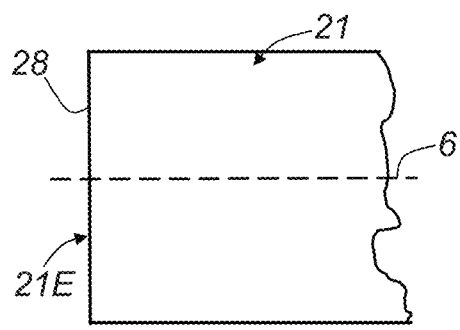
FIG. 13 is a sectional view of the first slider or third slider along its longitudinal axis.

FIG. 11 shows a sectional view of the second slider 22 transversely with respect to the plunger 24. The second slider 22 has a surface 26 against which the surface 28 rests against the free end 27 of the first slider 21 (see FIG. 13 and FIG. 14).

Figure 12:
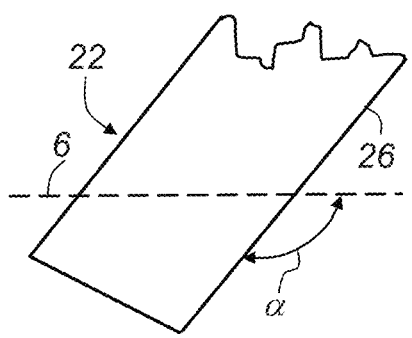
FIG. 12 is a side view of the second slider.
Figure 14:
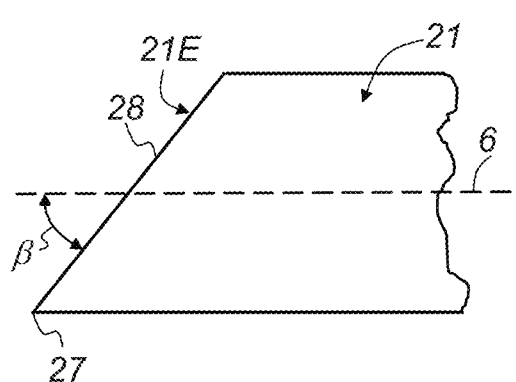
FIG. 14 is a side view of the first slider or third slider.

FIG. 12 shows a side view of the second slider 22. The surface 26 of the second slider 22 is inclined by an angle α with respect to the axis 6. Accordingly, as shown in FIG. 14, the slanted surface 28 of the first slider 21 is inclined with respect to the axis 6 by the angle β, which is complemented in sum by the angle α to 180°. When the second slider 22 is now inserted into the tool block 25 and the first slider 21 is pushed completely into the tool block 25, the surface 26 of the second slider 22 and the slanted surface 28 of the first slider 21 are abutted against one another by their entire surfaces 26, 28 and thereby ensure that no plastic material enters the interior of the basic body 4.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A tool for producing an injection device, the tool comprising:
   a tool block;
   a receptacle for a hollow needle, the receptacle being formed in the tool block;
   a first guide for at least one first slider formed in the tool block; and
   a second guide for a second slider formed in the tool block,
   wherein the first slider and the second slider together with the tool block substantially determine a shape of a pre-injection molded part of a basic body of the injection device,
   wherein the second slider, in a state of being inserted into the tool block, covers an end of the hollow needle inserted in the receptacle, and
   wherein the first slider comprises a flat front end and wherein an entire surface of the flat front end rests against a surface of the second slider when the first slider and the second slider are inserted in the tool block.

2. The tool as claimed in claim 1, wherein the second slider is configured such that, in a pushed-in state, the second slider surrounds and thus seals an end of the hollow needle inserted in the receptacle.

3. The tool as claimed in claim 1, wherein a plunger is guided in the second slider, which acts on an end of the hollow needle and pushes the hollow needle into a target position predetermined in the tool block, thereby sealing the end of the hollow needle.

4. The tool as claimed in claim 1, wherein a third slider is insertable into the first guide such that after removal of the second slider from the tool and thus from the basic body of the pre-injection molded part of the injection device, an opening formed by the second slider in the basic body is covered by the third slider from the interior of the basic body.

5. The tool as claimed in claim 4, wherein a flat front end of the third slider is formed by a slanted surface, and wherein a front free end of the third slider protrudes a front edge of the opening.

6. The tool as claimed in claim 1, wherein the first slider is rotatable in the first guide such that, after removal of the second slider from the tool and thus from the basic body of the injection device, an opening formed in the basic body by the second slider is covered by the rotated first slider from the interior of the basic body.

7. The tool as claimed in claim 6, wherein the first slider is rotatable about 180° so that a front free end of the first slider abuts against a front, inner wall of the basic body and thus seals the opening from the outside.

8. The tool as claimed in claim 6, wherein the flat front end of the first slider is formed by a slanted surface, and wherein the front free end of the first slider protrudes a front edge of the opening.

9. A method for producing an injection device, the method comprising:
   inserting a hollow needle into a receptacle in a tool block of a tool;
   inserting a second slider in an axial direction of the hollow needle, so that the second slider covers and seals an end of the hollow needle positioned in the receptacle;
   inserting a first slider as far as it rests with a flat front end thereof against a surface of the second slider;
   forming a pre-injection molded part of a basic body of the injection device by injecting a plastic material into the tool;
   removing the second slider from the tool such that an opening is formed in the pre-injection molded part of the basic body;

providing a sealing geometry, so that the opening in the basic body is covered; and closing the opening, by injecting plastic material into the tool.

10. The method as claimed in claim 9, wherein a plunger is guided in the second slider and acts on the end of the hollow needle such that the hollow needle is pushed into a target position predetermined in the tool block and also the end of the hollow needle is sealed.

11. The method as claimed in claim 9, wherein the first slider has a flat front end which, with its entire surface, rests against a surface of the second slider when the first slider is pushed into the tool as far as to the second slider, and wherein the surface of the second slider forms a stop for the first slider.

12. The method as claimed in claim 9, wherein the surface of the second slider rests sealingly on the flat front end of the first slider in such a way that during injection of the plastic material into the tool no plastic material can enter between the surface of the second slider and the flat front end of the first slider.

13. The method as claimed in claim 9, wherein a third slider, providing the sealing geometry, is inserted into the first guide after removal of the second slider from the tool, so that the opening formed by the second slider in the basic body of the pre-injection molded part of the injection device is covered from the interior of the basic body by the third slider.

14. The method as claimed in claim 13, wherein the sealing geometry is formed by a slanted surface of a flat front end of the third slider, and wherein a front free end of the third slider protrudes a front edge of the opening.

15. The method as claimed in claim 9, wherein after removal of the second slider from the tool, the first slider providing the sealing geometry is rotatable in the first guide such that, after the removal of the second slider from the tool the opening formed in the basic body after the removal of the second slider from the tool is covered from the interior of the basic body by the rotated first slider.

16. The method as claimed in claim 15, wherein the sealing geometry is formed by a slanted surface of a flat free end of the first slider, and wherein the front flat end of the first slider protrudes a front edge of the opening.

17. The tool as claimed in claim 1, wherein the entire surface of the flat front end of the first slider rests directly against the surface of the second slider.

18. The tool as claimed in claim 1, wherein the first slider is rotatable within the first guide.

* * * * *